(12) United States Patent
Hu et al.

(10) Patent No.: US 6,586,230 B1
(45) Date of Patent: Jul. 1, 2003

(54) HUMAN KINASE AND POLYNUCLEOTIDES ENCODING THE SAME

(75) Inventors: Yi Hu, Spring, TX (US); Boris Nepomnichy, Houston, TX (US); Brenda Gerhardt, Spring, TX (US); D. Wade Walke, Spring, TX (US); Carl Johan Friddle, The Woodlands, TX (US)

(73) Assignee: Lexicon Genetics Incorporated, The Woodlands, TX (US)

( * ) Notice: Subject to any disclaimer, the term of this patent is extended or adjusted under 35 U.S.C. 154(b) by 0 days.

(21) Appl. No.: 10/004,542

(22) Filed: Oct. 23, 2001

Related U.S. Application Data

(60) Provisional application No. 60/243,893, filed on Oct. 27, 2000.

(51) Int. Cl.$^7$ .......................... C12N 1/20; C12N 15/00; C12N 5/00; C12Q 1/68; C07H 21/04
(52) U.S. Cl. ................. 435/252.3; 435/194; 435/320.1; 435/325; 435/6; 536/23.2
(58) Field of Search ............................. 435/194, 320.1, 435/325, 252.3, 6; 536/23.2

(56) References Cited

U.S. PATENT DOCUMENTS

| | | | |
|---|---|---|---|
| 4,215,051 A | 7/1980 | Schroeder et al. | 260/346.7 |
| 4,376,110 A | 3/1983 | David et al. | 436/513 |
| 4,594,595 A | 6/1986 | Struckman | 343/770 |
| 4,631,211 A | 12/1986 | Houghten | 428/35 |
| 4,689,405 A | 8/1987 | Frank et al. | 536/27 |
| 4,713,326 A | 12/1987 | Dattagupta et al. | 435/6 |
| 4,873,191 A | 10/1989 | Wagner et al. | 435/172.3 |
| 4,946,778 A | 8/1990 | Ladner et al. | 435/64.9 |
| 5,252,743 A | 10/1993 | Barrett et al. | 548/303.7 |
| 5,272,057 A | 12/1993 | Smulson et al. | 435/6 |
| 5,424,186 A | 6/1995 | Fodor et al. | 435/6 |
| 5,445,934 A | 8/1995 | Fodor et al. | 435/6 |
| 5,459,127 A | 10/1995 | Felgner et al. | 514/7 |
| 5,556,752 A | 9/1996 | Lockhart et al. | 435/6 |
| 5,700,637 A | 12/1997 | Southern | 435/6 |
| 5,723,323 A | 3/1998 | Kauffman et al. | 435/172.3 |
| 5,744,305 A | 4/1998 | Fodor et al. | 435/6 |
| 5,830,721 A | 11/1998 | Stemmer et al. | 435/172.3 |
| 5,837,458 A | 11/1998 | Minshull et al. | 435/6 |
| 5,843,749 A | * 12/1998 | Maisopierre et al. | 435/194 |
| 5,869,336 A | 2/1999 | Meyer et al. | 435/348 |
| 5,877,397 A | 3/1999 | Lonberg et al. | 800/2 |
| 5,948,767 A | 9/1999 | Scheule et al. | 514/44 |
| 6,075,181 A | 6/2000 | Kucherlapati et al. | 800/25 |
| 6,110,490 A | 8/2000 | Thierry | 424/450 |
| 6,117,679 A | 9/2000 | Stemmer | 435/440 |
| 6,150,584 A | 11/2000 | Kucherlapati et al. | 800/8 |

OTHER PUBLICATIONS

Ottenwaelder et al., Database PIR 71, Accession No. T43450, Jan. 2000.*
Bird et al, 1988, "Single–Chain Antigen–Binding Proteins", Science 242:423–426.
Bitter et al, 1987, "Expression and Secretion Vectors for Yeast", Methods in Enzymology 153:516–544.
Colbere–Garapin et al, 1981, "A New Dominant Hybrid Selective Marker for Higher Eukaryotic Cells", J. Mol. Biol. 150:1–14.
Gautier et al, 1987, "α–DNA IV: α–anomeric and β–anomeric tetrathymidylates covalently linked to intercalating oxazolopyridocarbazole. Synthesis, physiochemical properties and poly (rA) binding", Nucleic Acids Research 15(16):6625–6641.
Gordon, 1989, "Transgenic Animals", International Review of Cytology, 115:171–229.
Greenspan et al, 1993, "Idiotypes: structure and immunogenicity", FASEB Journal 7:437–444.
Gu et al, 1994, "Delection of a DNA Polymerase β Gene Segment in T Cells Using Cell Type–Specific Gene Targeting", Science 265:103–106.
Huse et al, 1989, "Generation of a Large Combinatorial Library of the Immunoglobulin Repertoire in Phage Lambda", Science 246:1275–1281.
Huston et al, 1988, "Protein engineering of antibody binding sites: Recovery of specific activity in an anti–digoxin single–chain Fv analogue produced in *Escherichia coli*", Proc. Natl. Acad. Sci. USA 85:5879–5883.
Inoue et al, 1987, "Sequence–dependent hydrolysis of RNA using modified oligonucleotide splints and R Nase H", FEBS Letters 215(2):327–330.
Inoue et al, 1987, "Synthesis and hybridization studies on two complementary nona(2'–O–methyl)ribonucleotides", Nucleic Acids Research 15(15):6131–6149.
Inouye & Inouye, 1985, "Up–promoter mutations in the Ipp gene of *Escherichia coli*", Nucleic Acids Research 13(9):3101–3110.
Janknecht et al, 1991, "Rapid and efficient purification of native histidine–tagged protein expressed by recombinant vaccinia virus", PNAS U.S.A. 88:8972–8976.
Kohler & Milstein, 1975, "Continuous cultures of fused cells secreting antibody of predefined specificity", Nature 256:495–497.
Lakso et al, 1992, "Targeted oncogene activation by site–specific recombination in transgenic mice", Proc. Natl. Acad. Sci. USA 89:6232–6236.
Lavitrano et al, 1989, "Sperm Cells as Vectors for Introducing Foreign DNA into Eggs: Genetic Transformation of Mice", Cell 57:717–723.
Lo, 1983, "Transformation by Iontophoretic Microinjection of DNA: Multiple Integrations without Tandem Insertions", Mol. & Cell. Biology 3(10):1803–1814.

(List continued on next page.)

Primary Examiner—M. Monshipouri

(57) ABSTRACT

Novel human polynucleotide and polypeptide sequences are disclosed that can be used in therapeutic, diagnostic, and pharmacogenomic applications.

6 Claims, No Drawings

OTHER PUBLICATIONS

Logan et al, 1984, "Andenovirus tripartite leader sequence enhances translation of mRNAs late after infection", Proc. Natl. Acad. Sci. USA 81:3655–3659.

Lowy et al, 1980, "Isolation of Transforming DNA: Cloning the Hamster aprt Gene", Cell 22:817–823.

Morrison et al, 1984, "Chimeric human antibody molecules: Mouse antigen–binding domains with human constant region domains", Proc. Natl. Acad. Sci. USA 81:6851–6855.

Mulligan & Berg, 1981, "Selection for animal cells that express the *Escherichia coli* gene coding fo xanthine–guanine phosphoribosyltransferase", Proc. Natl. Acad. Sci. USA 78(4):2072–2076.

Neuberger et al, 1984, "Recombinant antibodies possessing novel effector functions", Nature 312:604–608.

Nisonoff, 1991, "Idiotypes: Concepts and Applications", J. of Immunology 147:2429–2438.

O'Hare et al, 1981, "Transformation of mouse fibroblasts to methotrexate resistance by a recombinant plasmid expressing a prokaryotic dihydrofolate reductase", Proc. Natl. Acad. Sci. USA 78(3):1527–1531.

Ruther et al, 1983, "Easy identification of cDNA clones", EMBO Journal 2(10):1791–1794.

Santerre et al, 1984, "Expression of prokaryotic genes for hygromycin B and G418 resistance as dominant–selection markers in mouse L cells", Gene 30:147–156.

Sarin et al, 1988, "Inhibition of acquired immunodeficiency syndrome virus by oligodeoxynucleoside methylphosphonates", Proc. Natl. Acad. Sci. USA 85:7448–7451.

Smith et al, 1983, "Molecular Engineering of the Autographa californica Nuclear Polyhedrosis Virus Genome: Deletion Mutations with the Polyhedrin Gene", J. Virol. 46(2):584–593.

Stein et al, 1988, "Physiochemical properties of phosphorothioate oligodeoxynucleotides", Nucleic Acids Research 16(8):3209–3221.

Szybalska & Szybalski, 1962, "Genetics of Human Cell Lines, IV. DNA–Mediated Heritable Transformation of a Biochemcial Trait", Proc. Natl. Acad. Sci. USA 48:2026–2034.

Takeda et al, 1985, "Construction of chimaeric processed immunoglobulin genes containing mouse variable and human constant region sequences", Nature 314:452–454.

Thompson et al, 1989, "Germ Line Transmission and Expression of a Corrected HPRT Gene Produced by Gene Targeting in Embryonic Stem Cells", Cell 56:313–321.

Van Der Putten et al, 1985, "Efficient insertion of genes into the mouse germ line via retroviral vectors", Proc. Natl. Acad. Sci. USA 82:6148–6152.

Van Heeke et al, 1989, "Expression of Human Asparagine Synthetase in *Escherichia coli*", J. Biol. Chemistry 264(10):5503–5509.

Ward et al, 1989, "Binding activities of a repertoire of single immunoglobulin variable domains secreted from *Escherichia coli*", Nature 341:544–546.

Wigler et al, 1977, "Transfer of Purified Herpes Virus Thymidine Kinase Gene to Cultured Mouse Cells", Cell 11:223–232.

Wigler et al, 1980, "Transformation of mammalian cells with an amplifiable dominant–acting gene", Proc. Natl. Acad. Sci. USA 77(6):3567–3570.

* cited by examiner

HUMAN KINASE AND POLYNUCLEOTIDES ENCODING THE SAME

The present application claims the benefit of U.S. Provisional Application No. 60/243,893, which was filed on Oct. 27, 2000 and is herein incorporated by reference in its entirety.

1. INTRODUCTION

The present invention relates to the discovery, identification, and characterization of novel human polynucleotides encoding proteins sharing sequence similarity with animal kinases. The invention encompasses the described polynucleotides, host cell expression systems, the encoded proteins, fusion proteins, polypeptides and peptides, antibodies to the encoded proteins and peptides, and genetically engineered animals that either lack or over express the disclosed genes, antagonists and agonists of the proteins, and other compounds that modulate the expression or activity of the proteins encoded by the disclosed genes that can be used for diagnosis, drug screening, clinical trial monitoring, the treatment of diseases and disorders, and cosmetic or nutriceutical applications.

2. BACKGROUND OF THE INVENTION

Kinases mediate the phosphorylation of a wide variety of proteins and compounds in the cell. Along with phosphatases, kinases are involved in a range of regulatory pathways. Given the physiological importance of kinases, they have been subject to intense scrutiny and are proven drug targets.

3. SUMMARY OF THE INVENTION

The present invention relates to the discovery, identification, and characterization of nucleotides that encode novel human proteins and the corresponding amino acid sequences of these proteins. The novel human proteins (NHPs) described for the first time herein share structural similarity with animal kinases, including, but not limited to, receptor tyrosine kinases. The NHPs exhibit particular similarity to ephrin-receptor family kinases. Accordingly, the described NHPS encode novel kinases having homologues and orthologs across a range of phyla and species.

The novel human polynucleotides described herein, encode open reading frames (ORFs) encoding proteins of 942 and 308 amino acids in length (see respectively SEQ ID NOS:2 and 4).

The invention also encompasses agonists and antagonists of the described NHPs, including small molecules, large molecules, mutant NHPs, or portions thereof, that compete with native NHP, peptides, and antibodies, as well as nucleotide sequences that can be used to inhibit the expression of the described NHPs (e.g., antisense and ribozyme molecules, and open reading frame or regulatory sequence replacement constructs) or to enhance the expression of the described NHPs (e.g., expression constructs that place the described polynucleotide under the control of a strong promoter system), and transgenic animals that express a NHP sequence, or "knock-outs" (which can be conditional) that do not express a functional NHP. Knock-out mice can be produced in several ways, one of which involves the use of mouse embryonic stem cells ("ES cells") lines that contain gene trap mutations in a murine homolog of at least one of the described NHPS. When the unique NHP sequences described in SEQ ID NOS:1–5 are "knocked-out" they provide a method of identifying phenotypic expression of the particular gene as well as a method of assigning function to previously unknown genes. In addition, animals in which the unique NHP sequences described in SEQ ID NOS:1–5 are "knocked-out" provide a unique source in which to elicit antibodies to homologous and orthologous proteins, which would have been previously viewed by the immune system as "self" and therefore would have failed to elicit significant antibody responses. To these ends, gene trapped knockout ES cells have been generated in murine homologs of the described NHPs.

Additionally, the unique NHP sequences described in SEQ ID NOS:1–5 are useful for the identification of protein coding sequence and mapping a unique gene to a particular chromosome (the exons encoding the described sequences are apparently encoded on human chromosome 3, see GENBANK accession no. AC027483). These sequences identify biologically verified exon splice junctions as opposed to splice junctions that may have merely been predicted from bioinformatics analysis of genomic sequence alone. The sequences of the present invention are also useful as additional DNA markers for restriction fragment length polymorphism (RFLP) analysis, and in forensic biology.

Further, the present invention also relates to processes for identifying compounds that modulate, i.e., act as agonists or antagonists, of NHP expression and/or NHP activity that utilize purified preparations of the described NHPs and/or NHP product, or cells expressing the same. Such compounds can be used as therapeutic agents for the treatment of any of a wide variety of symptoms associated with biological disorders or imbalances.

4. DESCRIPTION OF THE SEQUENCE LISTING AND FIGURES

The Sequence Listing provides the sequence of the novel human ORFs encoding the described novel human kinase proteins. SEQ ID NO:5 describes a NHP ORF and flanking sequences.

5. DETAILED DESCRIPTION OF THE INVENTION

The NHPs described for the first time herein are novel proteins that are expressed in, inter alia, human cell lines and human fetal brain, brain, pituitary, spinal cord, cerebellum, trachea, kidney, fetal liver, liver, prostate, testis, thyroid, stomach, small intestine, colon, uterus, adipose, esophagus, bladder, cervix, and pericardium cells.

The described sequences were compiled from sequences available in GENBANK, and cDNAs generated from prostate and testis mRNAs (Edge Biosystems, Gaithersburg, Md.).

The present invention encompasses the nucleotides presented in the Sequence Listing, host cells expressing such nucleotides, the expression products of such nucleotides, and: (a) nucleotides that encode mammalian homologs of the described genes, including the specifically described NHPs, and the NHP products; (b) nucleotides that encode one or more portions of an NHP that correspond to functional domains, and the polypeptide products specified by such nucleotide sequences, including, but not limited to, the novel regions of any active domain(s); (c) isolated nucleotides that encode mutant versions, engineered or naturally occurring, of the described NHPs in which all or a part of at least one domain is deleted or altered, and the polypeptide products specified by such nucleotide sequences, including, but not limited to, soluble proteins and peptides in which all or a portion of the signal sequence is deleted; (d) nucleotides that encode chimeric fusion proteins containing all or a portion of a coding region of a NHP, or one of its domains (e.g., a receptor/ligand binding domain, accessory protein/self-association domain, etc.) fused to another peptide or polypeptide; or (e) therapeutic or diagnostic derivatives of the described polynucleotides such as oligonucleotides, antisense polynucleotides, ribozymes, dsRNA, or gene therapy constructs comprising a sequence first disclosed in the Sequence Listing. As discussed above, the present invention includes: (a) the human DNA sequences presented in the Sequence Listing (and vectors comprising the same) and additionally contemplates any nucleotide sequence encoding a contiguous NHP open reading frame (ORF) that hybridizes to a complement of a DNA sequence presented in the Sequence Listing under highly stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel et al., eds., 1989, Current Protocols in Molecular Biology, Vol. I, Green Publishing Associates, Inc., and John Wiley & Sons, Inc., New York, at p. 2.10.3) and encodes a functionally equivalent expression product. Additionally, contemplated are any nucleotide sequences that hybridize to the complement of the DNA sequence that encode and express an amino acid sequence presented in the Sequence Listing under moderately stringent conditions, e.g., washing in 0.2×SSC/0.1% SDS at 42° C. (Ausubel et al., 1989, supra), yet still encode a functionally equivalent NHP product. Functional equivalents of a NHP include naturally occurring NHPs present in other species and mutant NHPs whether naturally occurring or engineered (by site directed mutagenesis, gene shuffling, directed evolution as described in, for example, U.S. Pat. No. 5,837,458 or 5,723,323 both of which are herein incorporated by reference). The invention also includes degenerate nucleic acid variants of the disclosed NHP polynucleotide sequences.

Additionally contemplated are polynucleotides encoding NHP ORFs, or their functional equivalents, encoded by polynucleotide sequences that are about 99, 95, 90, or about 85 percent similar to corresponding regions of a NHP (as measured by BLAST sequence comparison analysis using, for example, the GCG sequence analysis package using default parameters).

The invention also includes nucleic acid molecules, preferably DNA molecules, that hybridize to, and are therefore the complements of, the described NHP encoding polynucleotides. Such hybridization conditions can be highly stringent or less highly stringent, as described above. In instances where the nucleic acid molecules are deoxyoligonucleotides ("DNA oligos"), such molecules are generally about 16 to about 100 bases long, or about 20 to about 80, or about 34 to about 45 bases long, or any variation or combination of sizes represented therein that incorporate a contiguous region of sequence first disclosed in the Sequence Listing. Such oligonucleotides can be used in conjunction with the polymerase chain reaction (PCR) to screen libraries, isolate clones, and prepare cloning and sequencing templates, etc.

Alternatively, such NHP oligonucleotides can be used as hybridization probes for screening libraries, and assessing gene expression patterns (particularly using a micro array or high-throughput "chip" format). Additionally, a series of the described NHP oligonucleotide sequences, or the complements thereof, can be used to represent all or a portion of the described NHP sequences. An oligonucleotide or polynucleotide sequence first disclosed in at least a portion of one or more of the sequences of SEQ ID NOS:1–5 can be used as a hybridization probe in conjunction with a solid support matrix/substrate (resins, beads, membranes, plastics, polymers, metal or metallized substrates, crystalline or polycrystalline substrates, etc.). Of particular note are spatially addressable arrays (i.e., gene chips, microtiter plates, etc.) of oligonucleotides and polynucleotides, or corresponding oligopeptides and polypeptides, wherein at least one of the biopolymers present on the spatially addressable array comprises an oligonucleotide or polynucleotide sequence first disclosed in at least one of the sequences of SEQ ID NOS:1–5, or an amino acid sequence encoded thereby. Methods for attaching biopolymers to, or synthesizing biopolymers on, solid support matrices, and conducting binding studies thereon are disclosed in, inter alia, U.S. Pat. Nos. 5,700,637, 5,556,752, 5,744,305, 4,631,211, 5,445,934, 5,252,743, 4,713,326, 5,424,186, and 4,689,405 the disclosures of which are herein incorporated by reference in their entirety.

Addressable arrays comprising sequences first disclosed in SEQ ID NOS:1–5 can be used to identify and characterize the temporal and tissue specific expression of a gene. These addressable arrays incorporate oligonucleotide sequences of sufficient length to confer the required specificity, yet be within the limitations of the production technology. The length of these probes is within a range of between about 8 to about 2000 nucleotides. Preferably the probes consist of 60 nucleotides and more preferably 25 nucleotides from the sequences first disclosed in SEQ ID NOS:1–5.

For example, a series of the described oligonucleotide sequences, or the complements thereof, can be used in chip format to represent all or a portion of the described sequences. The oligonucleotides, typically between about 16 to about 40 (or any whole number within the stated range) nucleotides in length can partially overlap each other and/or the sequence may be represented using oligonucleotides that do not overlap. Accordingly, the described polynucleotide sequences shall typically comprise at least about two or three distinct oligonucleotide sequences of at least about 8 nucleotides in length that are each first disclosed in the described Sequence Listing. Such oligonucleotide sequences can begin at any nucleotide present within a sequence in the Sequence Listing and proceed in either a sense (5'-to-3') orientation vis-a-vis the described sequence or in an antisense orientation.

Microarray-based analysis allows the discovery of broad patterns of genetic activity, providing new understanding of gene functions and generating novel and unexpected insight into transcriptional processes and biological mechanisms. The use of addressable arrays comprising sequences first disclosed in SEQ ID NOS:1–5 provides detailed information about transcriptional changes involved in a specific pathway, potentially leading to the identification of novel components or gene functions that manifest themselves as novel phenotypes.

Probes consisting of sequences first disclosed in SEQ ID NOS:1–5 can also be used in the identification, selection and validation of novel molecular targets for drug discovery. The use of these unique sequences permits the direct confirmation of drug targets and recognition of drug dependent changes in gene expression that are modulated through pathways distinct from the drugs intended target. These unique sequences therefore also have utility in defining and monitoring both drug action and toxicity.

As an example of utility, the sequences first disclosed in SEQ ID NOS:1–5 can be utilized in microarrays or other assay formats, to screen collections of genetic material from patients who have a particular medical condition. These investigations can also be carried out using the sequences first disclosed in SEQ ID NOS:1–5 in silico and by comparing previously collected genetic databases and the disclosed sequences using computer software known to those in the art.

Thus the sequences first disclosed in SEQ ID NOS:1–5 can be used to identify mutations associated with a particular disease and also as a diagnostic or prognostic assay.

Although the presently described sequences have been specifically described using nucleotide sequence, it should be appreciated that each of the sequences can uniquely be described using any of a wide variety of additional structural attributes, or combinations thereof. For example, a given sequence can be described by the net composition of the nucleotides present within a given region of the sequence in conjunction with the presence of one or more specific oligonucleotide sequence(s) first disclosed in the SEQ ID NOS:1–5. Alternatively, a restriction map specifying the relative positions of restriction endonuclease digestion sites, or various palindromic or other specific oligonucleotide sequences can be used to structurally describe a given sequence. Such restriction maps, which are typically generated by widely available computer programs (e.g., the University of Wisconsin GCG sequence analysis package, SEQUENCHER 3.0, Gene Codes Corp., Ann Arbor, Mich., etc.), can optionally be used in conjunction with one or more discrete nucleotide sequence(s) present in the sequence that can be described by the relative position of the sequence relative to one or more additional sequence(s) or one or more restriction sites present in the disclosed sequence.

For oligonucleotide probes, highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as NHP gene antisense molecules, useful, for example, in NHP gene regulation (for and/or as antisense primers in amplification reactions of NHP gene nucleic acid sequences). With respect to NHP gene regulation, such techniques can be used to regulate biological functions. Further, such sequences can be used as part of ribozyme and/or triple helix sequences that are also useful for NHP gene regulation.

Inhibitory antisense or double stranded oligonucleotides can additionally comprise at least one modified base moiety that is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide can also comprise at least one modified sugar moiety selected from the group including, but not limited to, arabinose, 2-fluoroarabinose, xylulose, and hexose.

In yet another embodiment, the antisense oligonucleotide will comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-O-methylribonucleotide (Inoue et al., 1987, Nucl. Acids Res. 15:6131–6148), or a chimeric RNA-DNA analogue (Inoue et al., 1987, FEBS Lett. 215:327–330). Alternatively, double stranded RNA can be used to disrupt the expression and function of a targeted NHP.

Oligonucleotides of the invention can be synthesized by standard methods known in the art, e.g., by use of an automated DNA synthesizer (such as are commercially available from Biosearch, Applied Biosystems, etc.). As examples, phosphorothioate oligonucleotides can be synthesized by the method of Stein et al. (1988, Nucl. Acids Res. 16:3209), and methylphosphonate oligonucleotides can be prepared by use of controlled pore glass polymer supports (Sarin et al., 1988, Proc. Natl. Acad. Sci. U.S.A. 85:7448–7451), etc.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual (and periodic updates thereof), Cold Springs Harbor Press, N.Y.; and Ausubel et al., 1989, supra.

Alternatively, suitably labeled NHP nucleotide probes can be used to screen a human genomic library using appropriately stringent conditions or by PCR. The identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

For example, the present sequences can be used in restriction fragment length polymorphism (RFLP) analysis to identify specific individuals. In this technique, an individual's genomic DNA is digested with one or more restriction enzymes, and probed on a Southern blot to yield unique bands for identification (as generally described in U.S. Pat. No. 5,272,057, incorporated herein by reference). In addition, the sequences of the present invention can be used to provide polynucleotide reagents, e.g., PCR primers, targeted to specific loci in the human genome, which can enhance the reliability of DNA-based forensic identifications by, for example, providing another "identification marker" (i.e., another DNA sequence that is unique to a particular individual). Actual base sequence information can be used for identification as an accurate alternative to patterns formed by restriction enzyme generated fragments.

Further, a NHP gene homolog can be isolated from nucleic acid from an organism of interest by performing PCR using two degenerate or "wobble" oligonucleotide primer pools designed on the basis of amino acid sequences within the NHP products disclosed herein. The template for the reaction may be total RNA, mRNA, and/or cDNA obtained by reverse transcription of mRNA prepared from, for example, human or non-human cell lines or tissue known or suspected to express an allele of a NHP gene.

The PCR product can be subcloned and sequenced to ensure that the amplified sequences represent the sequence of the desired NHP gene. The PCR fragment can then be used to isolate a full length cDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library.

PCR technology can also be used to isolate full length cDNA sequences. For example, RNA can be isolated, following standard procedures, from an appropriate cellular or tissue source (i.e., one known, or suspected, to express a NHP gene). A reverse transcription (RT) reaction can be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment can be isolated. For a review of cloning strategies that can be used, see e.g., Sambrook et al., 1989, supra.

A cDNA encoding a mutant NHP sequence can be isolated, for example, by using PCR. In this case, the first cDNA strand may be synthesized by hybridizing an oligo-dT oligonucleotide to mRNA isolated from tissue known or suspected to be expressed in an individual putatively carrying a mutant NHP allele, and by extending the new strand with reverse transcriptase. The second strand of the cDNA is then synthesized using an oligonucleotide that hybridizes specifically to the 5' end of the normal sequence. Using these two primers, the product is then amplified via PCR, optionally cloned into a suitable vector, and subjected to DNA sequence analysis through methods well known to those of skill in the art. By comparing the DNA sequence of the mutant NHP allele to that of a corresponding normal NHP allele, the mutation(s) responsible for the loss or alteration of function of the mutant NHP gene product can be ascertained.

Alternatively, a genomic library can be constructed using DNA obtained from an individual suspected of or known to carry a mutant NHP allele (e.g., a person manifesting a NHP-associated phenotype such as, for example, immune disorders, obesity, high blood pressure, etc.), or a cDNA library can be constructed using RNA from a tissue known, or suspected, to express a mutant NHP allele. A normal NHP gene, or any suitable fragment thereof, can then be labeled and used as a probe to identify the corresponding mutant NHP allele in such libraries. Clones containing mutant NHP sequences can then be purified and subjected to sequence analysis according to methods well known to those skilled in the art.

Additionally, an expression library can be constructed utilizing cDNA synthesized from, for example, RNA isolated from a tissue known, or suspected, to express a mutant NHP allele in an individual suspected of or known to carry such a mutant allele. In this manner, gene products made by the putatively mutant tissue may be expressed and screened using standard antibody screening techniques in conjunction with antibodies raised against a normal NHP product, as described below (for screening techniques, see, for example, Harlow and Lane, eds., 1988, "Antibodies: A Laboratory Manual", Cold Spring Harbor Press, Cold Spring Harbor.) Additionally, screening can be accomplished by screening with labeled NHP fusion proteins, such as, for example, alkaline phosphatase-NHP or NHP-alkaline phosphatase fusion proteins. In cases where a NHP mutation results in an expression product with altered function (e.g., as a result of a missense or a frameshift mutation), polyclonal antibodies to NHP are likely to cross-react with a corresponding mutant NHP expression product. Library clones detected via their reaction with such labeled antibodies can be purified and subjected to sequence analysis according to methods well known in the art.

An additional application of the described novel human polynucleotide sequences is their use in the molecular mutagenesis/evolution of proteins that are at least partially encoded by the described novel sequences using, for example, polynucleotide shuffling or related methodologies. Such approaches are described in U.S. Pat. Nos. 5,830,721, 5,837,458, 6,117,679, and 5,723,323, which are herein incorporated by reference in their entirety.

The invention also encompasses (a) DNA vectors that contain any of the foregoing NHP coding sequences and/or their complements (i.e., antisense); (b) DNA expression vectors that contain any of the foregoing NHP coding sequences operatively associated with a regulatory element that directs the expression of the coding sequences (for example, baculovirus as described in U.S. Pat. No. 5,869, 336 herein incorporated by reference); (c) genetically engineered host cells that contain any of the foregoing NHP coding sequences operatively associated with a regulatory element that directs the expression of the coding sequences in the host cell; and (d) genetically engineered host cells that express an endogenous NHP sequence under the control of an exogenously introduced regulatory element (i.e., gene activation). As used herein, regulatory elements include, but are not limited to, inducible and non-inducible promoters, enhancers, operators and other elements known to those skilled in the art that drive and regulate expression. Such regulatory elements include, but are not limited to, the cytomegalovirus (hCMV) immediate early gene, regulatable, viral elements (particularly retroviral LTR promoters), the early or late promoters of SV40 adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

Where, as in the present instance, some of the described NHP peptides or polypeptides are thought to be cytoplasmic or nuclear proteins (although processed forms or fragments can be secreted or membrane associated), expression systems can be engineered that produce soluble derivatives of a NHP (corresponding to a NHP extracellular and/or intracellular domains, or truncated polypeptides lacking one or more hydrophobic domains) and/or NHP fusion protein products (especially NHP-Ig fusion proteins, i.e., fusions of a NHP domain to an IgFc), NHP antibodies, and anti-idiotypic antibodies (including Fab fragments) that can be used in therapeutic applications. Preferably, the above expression systems are engineered to allow the desired peptide or polypeptide to be recovered from the culture media.

The present invention also encompasses antibodies and anti-idiotypic antibodies (including Fab fragments), antagonists and agonists of a NHP, as well as compounds or nucleotide constructs that inhibit expression of a NHP sequence (transcription factor inhibitors, antisense and ribozyme molecules, or open reading frame sequence or regulatory sequence replacement constructs), or promote the expression of a NHP (e.g., expression constructs in which NHP coding sequences are operatively associated with expression control elements such as promoters, promoter/enhancers, etc.).

The NHPs or NHP peptides, NHP fusion proteins, NHP nucleotide sequences, antibodies, antagonists and agonists can be useful for the detection of mutant NHPs or inappropriately expressed NHPs for the diagnosis of disease. The NHP proteins or peptides, NHP fusion proteins, NHP nucleotide sequences, host cell expression systems, antibodies, antagonists, agonists and genetically engineered cells and animals can be used for screening for drugs (or high throughput screening of combinatorial libraries) effective in the treatment of the symptomatic or phenotypic manifestations of perturbing the normal function of a NHP in the body. The use of engineered host cells and/or animals can offer an advantage in that such systems allow not only for the identification of compounds that bind to the endogenous receptor/ligand of a NHP, but can also identify compounds that trigger NHP-mediated activities or pathways.

Finally, the NHP products can be used as therapeutics. For example, soluble derivatives such as NHP peptides/domains corresponding to NHPs, NHP fusion protein products (especially NHP-Ig fusion proteins, i.e., fusions of a NHP, or a domain of a NHP, to an IgFc), NHP antibodies and anti-idiotypic antibodies (including Fab fragments), antagonists or agonists (including compounds that modulate or act on downstream targets in a NHP-mediated pathway) can be used to directly treat diseases or disorders. For instance, the administration of an effective amount of soluble NHP, or a NHP-IgFc fusion protein or an anti-idiotypic antibody (or its Fab) that mimics the NHP could activate or effectively antagonize the endogenous NHP or a protein interactive therewith. Nucleotide constructs encoding such NHP products can be used to genetically engineer host cells to express such products in vivo; these genetically engineered cells function as "bioreactors" in the body delivering a continuous supply of a NHP, a NHP peptide, or a NHP fusion protein to the body. Nucleotide constructs encoding functional NHPs, mutant NHPs, as well as antisense and ribozyme molecules can also be used in "gene therapy" approaches for the modulation of NHP expression. Thus, the invention also encompasses pharmaceutical formulations and methods for treating biological disorders.

Various aspects of the invention are described in greater detail in the subsections below.

5.1 The NHP Sequences

The cDNA sequences and corresponding deduced amino acid sequences of the described NHPs are presented in the Sequence Listing.

Expression analysis has provided evidence that the described NHPs can be expressed in a range of human tissues. In addition to ephrin-receptor family kinases, the described NHPs also share significant similarity to several additional kinase families, including kinases associated with signal transduction, from a variety of phyla and species.

An additional application of the described novel human polynucleotide sequences is their use in the molecular mutagenesis/evolution of proteins that are at least partially encoded by the described novel sequences using, for example, polynucleotide shuffling or related methodologies. Such approaches are described in U.S. Pat. Nos. 5,830,721 and 5,837,458, which are herein incorporated by reference in their entirety.

NHP gene products can also be expressed in transgenic animals. Animals of any species, including, but not limited to, worms, mice, rats, rabbits, guinea pigs, pigs, micro-pigs, birds, goats, and non-human primates, e.g., baboons, monkeys, and chimpanzees may be used to generate NHP transgenic animals.

Any technique known in the art may be used to introduce a NHP transgene into animals to produce the founder lines of transgenic animals. Such techniques include, but are not limited to, pronuclear microinjection (Hoppe and Wagner, 1989, U.S. Pat. No. 4,873,191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the NHP transgene in all their cells, as well as animals that carry the transgene in some, but not all their cells, i.e., mosaic animals or somatic cell transgenic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al., 1992, Proc. Natl. Acad. Sci. USA 89:6232–6236. The regulatory sequences required for such a cell-type specific activation will depend upon the particular cell type of interest, and will be apparent to those of skill in the art.

When it is desired that a NHP transgene be integrated into the chromosomal site of the endogenous NHP gene, gene targeting is preferred. Briefly, when such a technique is to be utilized, vectors containing some nucleotide sequences homologous to the endogenous NHP gene are designed for the purpose of integrating, via homologous recombination with chromosomal sequences, into and disrupting the function of the nucleotide sequence of the endogenous NHP gene (i.e., "knockout" animals).

The transgene can also be selectively introduced into a particular cell type, thus inactivating the endogenous NHP gene in only that cell type, by following, for example, the teaching of Gu et al., 1994, Science, 265:103–106. The regulatory sequences required for such a cell-type specific inactivation will depend upon the particular cell type of interest, and will be apparent to those of skill in the art.

Once transgenic animals have been generated, the expression of the recombinant NHP gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques that include, but are not limited to, Northern blot analysis of tissue samples obtained from the animal, in situ hybridization analysis, and RT-PCR. Samples of NHP gene-expressing tissue, may also be evaluated immunocytochemically using antibodies specific for the NHP transgene product.

5.2 NHPS and NHP Polypeptides

NHPs, NHP polypeptides, NHP peptide fragments, mutated, truncated, or deleted forms of the NHPs, and/or NHP fusion proteins can be prepared for a variety of uses. These uses include, but are not limited to, the generation of antibodies, as reagents in diagnostic assays, for the identification of other cellular gene products related to a NHP, as reagents in assays for screening for compounds that can be used as pharmaceutical reagents useful in the therapeutic treatment of mental, biological, or medical disorders and disease. Given the similarity information and expression data, the described NHPs can be targeted (by drugs, oligos, antibodies, etc.) in order to treat disease, or to therapeutically augment the efficacy of therapeutic agents.

The Sequence Listing discloses the amino acid sequences encoded by the described NHP-encoding polynucleotides. The NHPs display initiator methionines that are present in DNA sequence contexts consistent with eucaryotic translation initiation sites. The NHPs do not display consensus signal sequences, which indicates that they may be cytoplasmic or possibly nuclear proteins, however, the homology data and presence of hydrophobic domains indicates that the NHPs are probably membrane associated, or possibly secreted.

The NHP amino acid sequences of the invention include the amino acid sequences presented in the Sequence Listing as well as analogues and derivatives thereof. Further, corresponding NHP homologues from other species are encompassed by the invention. In fact, any NHP protein encoded by the NHP nucleotide sequences described above are within the scope of the invention, as are any novel polynucleotide sequences encoding all or any novel portion of an amino acid sequence presented in the Sequence Listing. The degenerate nature of the genetic code is well known, and, accordingly, each amino acid presented in the Sequence Listing, is generically representative of the well known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biology", 1986, Darnell et al., eds., Scientific American Books, New York, N.Y., herein incorporated by reference) are generically representative of all the various permutations and combinations of nucleic acid sequences that can encode such amino acid sequences.

The invention also encompasses proteins that are functionally equivalent to the NHPs encoded by the presently described nucleotide sequences as judged by any of a number of criteria, including, but not limited to, the ability to bind and modify a NHP substrate, or the ability to effect an identical or complementary downstream pathway, or a change in cellular metabolism (e.g., proteolytic activity, ion flux, tyrosine phosphorylation, etc.). Such functionally equivalent NHP proteins include, but are not limited to, additions or substitutions of amino acid residues within the amino acid sequence encoded by the NHP nucleotide sequences described above, but that result in a silent change, thus producing a functionally equivalent expression product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

A variety of host-expression vector systems can be used to express the NHP nucleotide sequences of the invention. Where the NHP peptide or polypeptide can exist, or has been engineered to exist, as a soluble or secreted molecule, the soluble NHP peptide or polypeptide can be recovered from the culture media. Such expression systems also encompass engineered host cells that express a NHP, or functional equivalent, in situ. Purification or enrichment of a NHP from such expression systems can be accomplished using appropriate detergents and lipid micelles and methods well known to those skilled in the art. However, such engineered host cells themselves may be used in situations where it is important not only to retain the structural and functional characteristics of the NHP, but to assess biological activity, e.g., in drug screening assays.

The expression systems that may be used for purposes of the invention include, but are not limited to, microorganisms such as bacteria (e.g., *E. coli, B. subtilis*) transformed with recombinant bacteriophage DNA, plasmid DNA or cosmid DNA expression vectors containing NHP nucleotide sequences; yeast (e.g., Saccharomyces, Pichia) transformed with recombinant yeast expression vectors containing NHP nucleotide sequences; insect cell systems infected with recombinant virus expression vectors (e.g., baculovirus) containing NHP sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHP nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the NHP product being expressed. For example, when a large quantity of such a protein is to be produced for the generation of pharmaceutical compositions of or containing NHP, or for raising antibodies to a NHP, vectors that direct the expression of high levels of fusion protein products that are readily purified may be desirable. Such vectors include, but are not limited, to the *E. coli* expression vector pUR278 (Ruther et al., 1983, EMBO J. 2:1791), in which a NHP coding sequence may be ligated individually into the vector in frame with the lacZ coding region so that a fusion protein is produced; pIN vectors (Inouye and Inouye, 1985, Nucleic Acids Res. 13:3101–3109; Van Heeke and Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target expression product can be released from the GST moiety.

In an insect system, *Autographa californica* nuclear polyhedrosis virus (AcNPV) is used as a vector to express foreign polynucleotide sequences. The virus grows in *Spodoptera frugiperda* cells. A NHP coding sequence can be cloned individually into non-essential regions (for example the polyhedrin gene) of the virus and placed under control of an AcNPV promoter (for example the polyhedrin promoter). Successful insertion of NHP coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted sequence is expressed (e.g., see Smith et al., 1983, J. Virol. 46:584; Smith, U.S. Pat. No. 4,215,051).

In mammalian host cells, a number of viral-based expression systems may be utilized. In cases where an adenovirus is used as an expression vector, the NHP nucleotide sequence of interest may be ligated to an adenovirus transcription/translation control complex, e.g., the late promoter and tripartite leader sequence. This chimeric sequence may then be inserted in the adenovirus genome by in vitro or in vivo recombination. Insertion in a non-essential region of the viral genome (e.g., region E1 or E3) will result in a recombinant virus that is viable and capable of expressing a NHP product in infected hosts (e.g., See Logan and Shenk, 1984, Proc. Natl. Acad. Sci. USA 81:3655–3659). Specific initiation signals may also be required for efficient translation of inserted NHP nucleotide sequences. These signals include the ATG initiation codon and adjacent sequences. In cases where an entire NHP gene or cDNA, including its own initiation codon and adjacent sequences, is inserted into the appropriate expression vector, no additional translational control signals may be needed. However, in cases where only a portion of a NHP coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al., 1987, Methods in Enzymol. 153:516–544).

In addition, a host cell strain may be chosen that modulates the expression of the inserted sequences, or modifies and processes the expression product in the specific fashion desired. Such modifications (e.g., glycosylation) and processing (e.g., cleavage) of protein products may be important for the function of the protein. Different host cells have characteristic and specific mechanisms for the post-translational processing and modification of proteins and expression products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the expression product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines that stably express the NHP sequences described above can be engineered. Rather than using expression vectors that contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci, which in turn can be cloned and expanded into cell lines. This method may advantageously be used to engineer cell lines that express the NHP product. Such engineered cell lines may be particularly useful in screening and evaluation of compounds that affect the endogenous activity of the NHP product.

A number of selection systems may be used, including, but not limited to, the herpes simplex virus thymidine kinase (Wigler et al., 1977, Cell 11:223), hypoxanthine-guanine phosphoribosyltransferase (Szybalska and Szybalski, 1962, Proc. Natl. Acad. Sci. USA 48:2026), and adenine phosphoribosyltransferase (Lowy et al., 1980, Cell 22:817) genes, which can be employed in tk$^-$, hgprt$^-$ or aprt$^-$ cells, respectively. Also, antimetabolite resistance can be used as the basis of selection for the following genes: dhfr, which confers resistance to methotrexate (Wigler et al., 1980, Natl. Acad. Sci. USA 77:3567; O'Hare et al., 1981, Proc. Natl. Acad. Sci. USA 78:1527); gpt, which confers resistance to mycophenolic acid (Mulligan and Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30:147).

Alternatively, any fusion protein can be readily purified by utilizing an antibody specific for the fusion protein being expressed. For example, a system described by Janknecht et al. allows for the ready purification of non-denatured fusion proteins expressed in human cell lines (Janknecht et al., 1991, Proc. Natl. Acad. Sci. USA 88:8972–8976). In this system, the sequence of interest is subcloned into a vaccinia recombination plasmid such that the sequence's open reading frame is translationally fused to an amino-terminal tag consisting of six histidine residues. Extracts from cells infected with recombinant vaccinia virus are loaded onto Ni$^{2+}$.nitriloacetic acid-agarose columns and histidine-tagged proteins are selectively eluted with imidazole-containing buffers.

Also encompassed by the present invention are fusion proteins that direct the NHP to a target organ and/or facilitate transport across the membrane into the cytosol. Conjugation of NHPs to antibody molecules or their Fab fragments could be used to target cells bearing a particular epitope. Attaching the appropriate signal sequence to the NHP would also transport the NHP to the desired location within the cell. Alternatively targeting of NHP or its nucleic acid sequence might be achieved using liposome or lipid complex based delivery systems. Such technologies are described in "Liposomes: A Practical Approach", New, R.R.C., ed., Oxford University Press, New York, and in U.S. Pat. Nos. 4,594, 595, 5,459,127, 5,948,767 and 6,110,490 and their respective disclosures, which are herein incorporated by reference in their entirety. Additionally embodied are novel protein constructs engineered in such a way that they facilitate transport of the NHP to the target site or desired organ, where they cross the cell membrane and/or the nucleus where the NHP can exert its functional activity. This goal may be achieved by coupling of the NHP to a cytokine or other ligand that provides targeting specificity, and/or to a protein transducing domain (see generally U.S. Provisional Patent Application Ser. Nos. 60/111,701 and 60/056,713, both of which are herein incorporated by reference, for examples of such transducing sequences) to facilitate passage across cellular membranes and can optionally be engineered to include nuclear localization.

5.3 Antibodies to NHP Products

Antibodies that specifically recognize one or more epitopes of a NHP, or epitopes of conserved variants of a NHP, or peptide fragments of a NHP are also encompassed by the invention. Such antibodies include, but are not limited to, polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

The antibodies of the invention can be used, for example, in the detection of NHP in a biological sample and may, therefore, be utilized as part of a diagnostic or prognostic technique whereby patients may be tested for abnormal amounts of NHP. Such antibodies may also be utilized in conjunction with, for example, compound screening schemes for the evaluation of the effect of test compounds on expression and/or activity of a NHP expression product. Additionally, such antibodies can be used in conjunction gene therapy to, for example, evaluate the normal and/or engineered NHP-expressing cells prior to their introduction into the patient. Such antibodies may additionally be used as a method for the inhibition of abnormal NHP activity. Thus, such antibodies may, therefore, be utilized as part of treatment methods.

For the production of antibodies, various host animals may be immunized by injection with the NHP, a NHP peptide (e.g., one corresponding to a functional domain of a NHP), truncated NHP polypeptides (NHP in which one or more domains have been deleted), functional equivalents of the NHP or mutated variant of the NHP. Such host animals may include, but are not limited to, pigs, rabbits, mice, goats, and rats, to name but a few. Various adjuvants may be used to increase the immunological response, depending on the host species, including, but not limited to, Freund's adjuvant (complete and incomplete), mineral salts such as aluminum hydroxide or aluminum phosphate, chitosan, surface active substances such as lysolecithin, pluronic polyols, polyanions, peptides, oil emulsions, and potentially useful human adjuvants such as BCG (bacille Calmette-Guerin) and *Corynebacterium parvum*. Alternatively, the immune response could be enhanced by combination and or coupling with molecules such as keyhole limpet hemocyanin, tetanus toxoid, diphtheria toxoid, ovalbumin, cholera toxin or fragments thereof. Polyclonal antibodies are heterogeneous populations of antibody molecules derived from the sera of the immunized animals.

Monoclonal antibodies, which are homogeneous populations of antibodies to a particular antigen, can be obtained by any technique that provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. Such technologies are described in U.S. Pat. Nos. 6,075,181 and 5,877,397 and their respective disclosures, which are herein incorporated by reference in their entirety. Also encompassed by the present invention is the use of fully humanized monoclonal antibodies as described in U.S. Pat. No. 6,150,584 and respective disclosures, which are herein incorporated by reference in their entirety.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 341:544–546) can be adapted to produce single chain antibodies against NHP expression products. Single chain antibodies are formed by linking the heavy and light chain fragments of the Fv region via an amino acid bridge, resulting in a single chain polypeptide.

Antibody fragments that recognize specific epitopes may be generated by known techniques. For example, such fragments include, but are not limited to, the F(ab')$_2$ fragments, which can be produced by pepsin digestion of the antibody molecule, and the Fab fragments, which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

Antibodies to a NHP can, in turn, be utilized to generate anti-idiotype antibodies that "mimic" a given NHP, using techniques well known to those skilled in the art (see, e.g., Greenspan and Bona, 1993, FASEB J 7:437–444; and Nissinoff, 1991, J. Immunol. 147:2429–2438). For example, antibodies that bind to a NHP domain and competitively inhibit the binding of NHP to its cognate receptor/ligand can be used to generate anti-idiotypes that "mimic" the NHP and, therefore, bind, activate, or neutralize a NHP, NHP receptor, or NHP ligand. Such anti-idiotypic antibodies or Fab fragments of such anti-idiotypes can be used in therapeutic regimens involving a NHP mediated pathway.

Additionally given the high degree of relatedness of mammalian NHPs, the presently described knock-out mice (having never seen NHP, and thus never been tolerized to NHP) have a unique utility, as they can be advantageously applied to the generation of antibodies against the disclosed mammalian NHP (i.e., NHP will be immunogenic in NHP knock-out animals).

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims. All cited publications, patents, and patent applications are herein incorporated by reference in their entirety.

What is claimed is:

1. An isolated nucleic acid molecule comprising the nucleotide sequence drawn from the group consisting of SEQ ID NO:1 and SEQ ID NO:3.

2. An isolated nucleic acid molecule comprising a nucleotide sequence that encodes the amino acid sequence shown in SEQ ID NO:2.

3. An isolated nucleic acid expression vector comprising a nucleotide sequence encoding the amino acid sequence of SEQ ID NO:2.

4. The expression vector of claim 3, werein said vector comprises the nucleotide sequence of SEQ ID NO:1.

5. An isolated nucleic acid expression vector comprising the nucleotide sequence of SEQ ID NO:3.

6. A host cell comprising the expression vector of claim 3, 4 or 5.

* * * * *

SEQUENCE LISTING

<160> NUMBER OF SEQ ID NOS: 5

<210> SEQ ID NO 1
<211> LENGTH: 2829
<212> TYPE: DNA
<213> ORGANISM: homo sapiens

<400> SEQUENCE: 1

| | | | | | |
|---|---|---|---|---|---|
| atgcaattcc | cctcgcctcc | agccgcgagg | agctccccgg | cgccgcaggc | agcgtcctcc | 60 |
| tccgaagcag | ctgcacctgc | aactgggcag | cctggaccct | cgtgccctgt | tcccgggacc | 120 |
| tcgcgcaggg | ggcgccccgg | gacaccccct | gcgggccggg | tggaggagga | agaggaggag | 180 |
| gaggaagaag | acgtggacaa | ggacccccat | cctacccaga | cacctgcct | gcgctgccgc | 240 |
| cacttctctt | taagggagag | gaaaagagag | cctaggagaa | ccatgggggg | ctgcgaagtc | 300 |
| cgggaatttc | ttttgcaatt | tggtttcttc | ttgcctctgc | tgacagcgtg | gccaggcgac | 360 |
| tgcagtcacg | tctccaacaa | ccaagttgtg | ttgcttgata | caacaactgt | actgggagag | 420 |
| ctaggatgga | aaacatatcc | attaaatggg | tgggatgcca | tcactgaaat | ggatgaacat | 480 |
| aataggccca | ttcacacata | ccaggtatgt | aatgtaatgg | aaccaaacca | aaacaactgg | 540 |
| cttcgtacaa | actggatctc | ccgtgatgca | gctcagaaaa | tttatgtgga | aatgaaattc | 600 |
| acactaaggg | attgtaacag | catcccatgg | gtcttgggga | cttgcaaaga | aacatttaat | 660 |
| ctgtttata | tggaatcaga | tgagtcccac | ggaattaaat | tcaagccaaa | ccagtataca | 720 |
| aagatcgaca | caattgctgc | tgatgagagt | tttacccaga | tggatttggg | tgatcgcatc | 780 |
| ctcaaactca | acactgaaat | tcgtgaggtg | gggcctatag | aaaggaaagg | attttatctg | 840 |
| gcttttcaag | acattgggc | gtgcattgcc | ctggtttcag | tccgtgtttt | ctacaagaaa | 900 |
| tgccccttca | ctgttcgtaa | cttggccatg | tttcctgata | ccattccaag | ggttgattcc | 960 |
| tcctctttgg | ttgaagcacg | gggttcttgt | gtgaagagtg | ctgaagagcg | tgacactcct | 1020 |
| aaactgtatt | gtggagctga | tggagattgg | ctggttcctc | ttggaaggtg | catctgcagt | 1080 |
| acaggatatg | aagaaattga | gggttcttgc | catgcttgca | gaccaggatt | ctataaagct | 1140 |
| tttgctggga | cacaaaaatg | ttctaaatgt | cctccacaca | gtttaacata | catggaagca | 1200 |
| acttctgtct | gtcagtgtga | aagggttat | ttccgagctg | aaaaagaccc | accttctatg | 1260 |
| gcatgtacca | ggccaccttc | agctcctagg | aatgtggttt | ttaacatcaa | tgaaacagcc | 1320 |
| cttattttgg | aatggagccc | accaagtgac | acaggaggga | gaaaagatct | cacatacagt | 1380 |
| gtaatctgta | agaaatgtgg | cttagacacc | agccagtgtg | aggactgtgg | tggaggactc | 1440 |
| cgcttcatcc | aagacatac | aggcctgatc | aacaattccg | tgatagtact | tgactttgtg | 1500 |
| tctcacgtga | attacacctt | tgaaatagaa | gcaatgaatg | gagtttctga | gttgagtttt | 1560 |
| tctcccaagc | cattcacagc | tattacagtg | accacggatc | aagatgcacc | ttccctgata | 1620 |
| ggtgtggtaa | ggaaggactg | ggcatcccaa | aatagcattg | ccctatcatg | gcaagcacct | 1680 |
| gcttttttcca | atggagccat | tctggactac | gagatcaagt | actatgagaa | agaacatgag | 1740 |
| cagctgacct | actcttccac | aaggtccaaa | gcccccagtg | tcatcatcac | aggtcttaag | 1800 |
| ccagccacca | aatatgtatt | tcacatccga | gtgagaactg | cgacaggata | cagtggctac | 1860 |
| agtcagaaat | ttgaatttga | aacaggagat | gaaacttctg | acatggcagc | agaacaagga | 1920 |
| cagattctcg | tgatagccac | cgccgctgtt | gggggattca | ctctcctcgt | catcctcact | 1980 |
| ttattcttct | tgatcactgg | gagatgtcag | tggtacataa | aagccaagat | gaagtcagaa | 2040 |

```
gagaagagaa gaaaccactt acagaatggg catttgcgct tcccgggaat taaaacttac    2100
attgatccag atacatatga agacccatcc ctagcagtcc atgaatttgc aaaggagatt    2160
gatccctcaa gaattcgtat tgagagagtc attggggcag gtgaatttgg agaagtctgt    2220
agtgggcgtt tgaagacacc agggaaaaga gagatcccag ttgccattaa aactttgaaa    2280
ggtggccaca tggatcggca agaagagat tttctaagag aagctagtat catgggccag     2340
tttgaccatc caaacatcat tcgcctagaa ggggttgtca ccaaaagatc cttcccggcc    2400
attggggtgg aggcgttttg ccccagcttc ctgagggcag ggttttttaaa tagcatccag   2460 gccccgcatc cagtgccagg gggaggatct ttgcccccca ggattcctgc tggcagacca    2520
gtaatgattg tggtggaata tatggagaat ggatccctag actccttttt gcggaagcat    2580
gatggccact tcacagtcat ccagttggtc ggaatgctcc gaggcattgc atcaggcatg    2640
aagtatcttt ctgatatggg ttatgttcat cgagacctag cggctcggaa tatactggtc    2700
aatagcaact tagtatgcaa agtttctgat tttggtctct ccagagtgct ggaagatgat    2760
ccagaagctg cttatacaac aactgacctc ttccaaactc taacacttaa cctctgctat    2820
tctgcataa                                                              2829

<210> SEQ ID NO 2
<211> LENGTH: 942
<212> TYPE: PRT
<213> ORGANISM: homo sapiens

<400> SEQUENCE: 2

Met Gln Phe Pro Ser Pro Pro Ala Ala Arg Ser Ser Pro Ala Pro Gln
 1               5                  10                  15

Ala Ala Ser Ser Ser Glu Ala Ala Ala Pro Ala Thr Gly Gln Pro Gly
                20                  25                  30

Pro Ser Cys Pro Val Pro Gly Thr Ser Arg Arg Gly Arg Pro Gly Thr
            35                  40                  45

Pro Pro Ala Gly Arg Val Glu Glu Glu Glu Glu Glu Glu Glu Glu Asp
        50                  55                  60

Val Asp Lys Asp Pro His Pro Thr Gln Asn Thr Cys Leu Arg Cys Arg
 65                  70                  75                  80

His Phe Ser Leu Arg Glu Arg Lys Arg Glu Pro Arg Arg Thr Met Gly
                85                  90                  95

Gly Cys Glu Val Arg Glu Phe Leu Leu Gln Phe Gly Phe Phe Leu Pro
               100                 105                 110

Leu Leu Thr Ala Trp Pro Gly Asp Cys Ser His Val Ser Asn Asn Gln
            115                 120                 125

Val Val Leu Leu Asp Thr Thr Thr Val Leu Gly Glu Leu Gly Trp Lys
        130                 135                 140

Thr Tyr Pro Leu Asn Gly Trp Asp Ala Ile Thr Glu Met Asp Glu His
145                 150                 155                 160

Asn Arg Pro Ile His Thr Tyr Gln Val Cys Asn Val Met Glu Pro Asn
                165                 170                 175

Gln Asn Asn Trp Leu Arg Thr Asn Trp Ile Ser Arg Asp Ala Ala Gln
            180                 185                 190

Lys Ile Tyr Val Glu Met Lys Phe Thr Leu Arg Asp Cys Asn Ser Ile
        195                 200                 205

Pro Trp Val Leu Gly Thr Cys Lys Glu Thr Phe Asn Leu Phe Tyr Met
    210                 215                 220
```

-continued

| | | | | | | | | | | | |
|---|---|---|---|---|---|---|---|---|---|---|---|
|Glu|Ser|Asp|Glu|Ser|His|Gly|Ile|Lys|Phe|Lys|Pro|Asn|Gln|Tyr|Thr
225| | | | |230| | | |235| | | | | |240

Lys Ile Asp Thr Ile Ala Ala Asp Glu Ser Phe Thr Gln Met Asp Leu
              245                 250                 255

Gly Asp Arg Ile Leu Lys Leu Asn Thr Glu Ile Arg Glu Val Gly Pro
              260                 265                 270

Ile Glu Arg Lys Gly Phe Tyr Leu Ala Phe Gln Asp Ile Gly Ala Cys
              275                 280                 285

Ile Ala Leu Val Ser Val Arg Val Phe Tyr Lys Lys Cys Pro Phe Thr
290                 295                 300

Val Arg Asn Leu Ala Met Phe Pro Asp Thr Ile Pro Arg Val Asp Ser
305                 310                 315                 320

Ser Ser Leu Val Glu Ala Arg Gly Ser Cys Val Lys Ser Ala Glu Glu
              325                 330                 335

Arg Asp Thr Pro Lys Leu Tyr Cys Gly Ala Asp Gly Asp Trp Leu Val
              340                 345                 350

Pro Leu Gly Arg Cys Ile Cys Ser Thr Gly Tyr Glu Glu Ile Glu Gly
              355                 360                 365

Ser Cys His Ala Cys Arg Pro Gly Phe Tyr Lys Ala Phe Ala Gly Asn
              370                 375                 380

Thr Lys Cys Ser Lys Cys Pro Pro His Ser Leu Thr Tyr Met Glu Ala
385                 390                 395                 400

Thr Ser Val Cys Gln Cys Glu Lys Gly Tyr Phe Arg Ala Glu Lys Asp
              405                 410                 415

Pro Pro Ser Met Ala Cys Thr Arg Pro Pro Ser Ala Pro Arg Asn Val
              420                 425                 430

Val Phe Asn Ile Asn Glu Thr Ala Leu Ile Leu Glu Trp Ser Pro Pro
              435                 440                 445

Ser Asp Thr Gly Gly Arg Lys Asp Leu Thr Tyr Ser Val Ile Cys Lys
              450                 455                 460

Lys Cys Gly Leu Asp Thr Ser Gln Cys Glu Asp Cys Gly Gly Gly Leu
465                 470                 475                 480

Arg Phe Ile Pro Arg His Thr Gly Leu Ile Asn Asn Ser Val Ile Val
              485                 490                 495

Leu Asp Phe Val Ser His Val Asn Tyr Thr Phe Glu Ile Glu Ala Met
              500                 505                 510

Asn Gly Val Ser Glu Leu Ser Phe Ser Pro Lys Pro Phe Thr Ala Ile
              515                 520                 525

Thr Val Thr Thr Asp Gln Asp Ala Pro Ser Leu Ile Gly Val Val Arg
              530                 535                 540

Lys Asp Trp Ala Ser Gln Asn Ser Ile Ala Leu Ser Trp Gln Ala Pro
545                 550                 555                 560

Ala Phe Ser Asn Gly Ala Ile Leu Asp Tyr Glu Ile Lys Tyr Tyr Glu
              565                 570                 575

Lys Glu His Glu Gln Leu Thr Tyr Ser Ser Thr Arg Ser Lys Ala Pro
              580                 585                 590

Ser Val Ile Ile Thr Gly Leu Lys Pro Ala Thr Lys Tyr Val Phe His
              595                 600                 605

Ile Arg Val Arg Thr Ala Thr Gly Tyr Ser Gly Tyr Ser Gln Lys Phe
              610                 615                 620

Glu Phe Glu Thr Gly Asp Glu Thr Ser Asp Met Ala Ala Glu Gln Gly
625                 630                 635                 640

-continued

```
Gln Ile Leu Val Ile Ala Thr Ala Ala Val Gly Gly Phe Thr Leu Leu
                645                 650                 655
Val Ile Leu Thr Leu Phe Phe Leu Ile Thr Gly Arg Cys Gln Trp Tyr
            660                 665                 670
Ile Lys Ala Lys Met Lys Ser Glu Glu Lys Arg Asn His Leu Gln
        675                 680                 685
Asn Gly His Leu Arg Phe Pro Gly Ile Lys Thr Tyr Ile Asp Pro Asp
    690                 695                 700
Thr Tyr Glu Asp Pro Ser Leu Ala Val His Glu Phe Ala Lys Glu Ile
705                 710                 715                 720
Asp Pro Ser Arg Ile Arg Ile Glu Arg Val Ile Gly Ala Gly Glu Phe
                725                 730                 735
Gly Glu Val Cys Ser Gly Arg Leu Lys Thr Pro Gly Lys Arg Glu Ile
            740                 745                 750
Pro Val Ala Ile Lys Thr Leu Lys Gly Gly His Met Asp Arg Gln Arg
        755                 760                 765
Arg Asp Phe Leu Arg Glu Ala Ser Ile Met Gly Gln Phe Asp His Pro
    770                 775                 780
Asn Ile Ile Arg Leu Glu Gly Val Val Thr Lys Arg Ser Phe Pro Ala
785                 790                 795                 800
Ile Gly Val Glu Ala Phe Cys Pro Ser Phe Leu Arg Ala Gly Phe Leu
                805                 810                 815
Asn Ser Ile Gln Ala Pro His Pro Val Pro Gly Gly Ser Leu Pro
            820                 825                 830
Pro Arg Ile Pro Ala Gly Arg Pro Val Met Ile Val Val Glu Tyr Met
        835                 840                 845
Glu Asn Gly Ser Leu Asp Ser Phe Leu Arg Lys His Asp Gly His Phe
    850                 855                 860
Thr Val Ile Gln Leu Val Gly Met Leu Arg Gly Ile Ala Ser Gly Met
865                 870                 875                 880
Lys Tyr Leu Ser Asp Met Gly Tyr Val His Arg Asp Leu Ala Ala Arg
                885                 890                 895
Asn Ile Leu Val Asn Ser Asn Leu Val Cys Lys Val Ser Asp Phe Gly
            900                 905                 910
Leu Ser Arg Val Leu Glu Asp Asp Pro Glu Ala Ala Tyr Thr Thr Thr
        915                 920                 925
Asp Leu Phe Gln Thr Leu Thr Leu Asn Leu Cys Tyr Ser Ala
    930                 935                 940

<210> SEQ ID NO 3
<211> LENGTH: 927
<212> TYPE: DNA
<213> ORGANISM: homo sapiens

<400> SEQUENCE: 3
atggcagcag aacaaggaca gattctcgtg atagccaccg ccgctgttgg gggattcact      60
ctcctcgtca tcctcacttt attcttcttg atcactggga gatgtcagtg gtacataaaa     120
gccaagatga agtcagaaga gaagagaaga accacttaca gaatgggca tttgcgcttc     180
ccgggaatta aaacttacat tgatccagat acatatgaag accatccct agcagtccat     240
gaatttgcaa aggagattga tccctcaaga attcgtattg agagagtcat tggggcaggt     300
gaatttggag aagtctgtag tgggcgtttg aagacaccag ggaaaagaga gatcccagtt     360
gccattaaaa ctttgaaagg tggccacatg gatcggcaaa gaagagattt tctaagagaa     420
```

-continued

```
gctagtatca tgggccagtt tgaccatcca acatcattc gcctagaagg ggttgtcacc      480
aaaagatcct tcccggccat tggggtggag gcgttttgcc ccagcttcct gagggcaggg      540 ttttaaata gcatccaggc cccgcatcca gtgccagggg gaggatcttt gccccccagg      600
attcctgctg gcagaccagt aatgattgtg gtggaatata tggagaatgg atccctagac      660 tccttttgc ggaagcatga tgccacttc acagtcatcc agttggtcgg aatgctccga      720
ggcattgcat caggcatgaa gtatctttct gatatgggtt atgttcatcg agacctagcg      780
gctcggaata tactggtcaa tagcaactta gtatgcaaag tttctgattt tggtctctcc      840
agagtgctgg aagatgatcc agaagctgct tatacaacaa ctgacctctt ccaaactcta      900
acacttaacc tctgctattc tgcataa                                          927
```

<210> SEQ ID NO 4
<211> LENGTH: 308
<212> TYPE: PRT
<213> ORGANISM: homo sapiens

<400> SEQUENCE: 4

```
Met Ala Ala Glu Gln Gly Gln Ile Leu Val Ile Ala Thr Ala Ala Val
 1               5                  10                  15

Gly Gly Phe Thr Leu Leu Val Ile Leu Thr Leu Phe Phe Leu Ile Thr
            20                  25                  30

Gly Arg Cys Gln Trp Tyr Ile Lys Ala Lys Met Lys Ser Glu Glu Lys
        35                  40                  45

Arg Arg Asn His Leu Gln Asn Gly His Leu Arg Phe Pro Gly Ile Lys
    50                  55                  60

Thr Tyr Ile Asp Pro Asp Thr Tyr Glu Asp Pro Ser Leu Ala Val His
65                  70                  75                  80

Glu Phe Ala Lys Glu Ile Asp Pro Ser Arg Ile Arg Ile Glu Arg Val
                85                  90                  95

Ile Gly Ala Gly Glu Phe Gly Glu Val Cys Ser Gly Arg Leu Lys Thr
            100                 105                 110

Pro Gly Lys Arg Glu Ile Pro Val Ala Ile Lys Thr Leu Lys Gly Gly
        115                 120                 125

His Met Asp Arg Gln Arg Arg Asp Phe Leu Arg Glu Ala Ser Ile Met
    130                 135                 140

Gly Gln Phe Asp His Pro Asn Ile Ile Arg Leu Glu Gly Val Val Thr
145                 150                 155                 160

Lys Arg Ser Phe Pro Ala Ile Gly Val Glu Ala Phe Cys Pro Ser Phe
                165                 170                 175

Leu Arg Ala Gly Phe Leu Asn Ser Ile Gln Ala Pro His Pro Val Pro
            180                 185                 190

Gly Gly Gly Ser Leu Pro Pro Arg Ile Pro Ala Gly Arg Pro Val Met
        195                 200                 205

Ile Val Val Glu Tyr Met Glu Asn Gly Ser Leu Asp Ser Phe Leu Arg
    210                 215                 220

Lys His Asp Gly His Phe Thr Val Ile Gln Leu Val Gly Met Leu Arg
225                 230                 235                 240

Gly Ile Ala Ser Gly Met Lys Tyr Leu Ser Asp Met Gly Tyr Val His
                245                 250                 255

Arg Asp Leu Ala Ala Arg Asn Ile Leu Val Asn Ser Asn Leu Val Cys
            260                 265                 270

Lys Val Ser Asp Phe Gly Leu Ser Arg Val Leu Glu Asp Asp Pro Glu
        275                 280                 285
```

```
Ala Ala Tyr Thr Thr Thr Asp Leu Phe Gln Thr Leu Thr Leu Asn Leu
    290                 295                 300

Cys Tyr Ser Ala
305

<210> SEQ ID NO 5
<211> LENGTH: 3220
<212> TYPE: DNA
<213> ORGANISM: homo sapiens

<400> SEQUENCE: 5
cggtcctcgc ggtgaggggc tccccgcccc ctcgctcccc tccccaaaac cacagcccga      60
gctcgttctt gcgcgcgcgc gctctctccg gcccaagtga atagtcctcg cgcaagtggg     120
acactgtggt ggatgcaatt cccctcgcct ccagccgcga ggagctcccc ggcgccgcag     180
gcagcgtcct cctccgaagc agctgcacct gcaactgggc agcctggacc ctcgtgccct     240
gttcccggga cctcgcgcag ggggcgcccc gggacacccc ctgcgggccg ggtggaggag     300
gaagaggagg aggaggaaga agacgtggac aaggacccc atcctaccca gaacacctgc      360
ctgcgctgcc gccacttctc tttaagggag aggaaaagag agcctaggag aaccatgggg     420
ggctgcgaag tccgggaatt tcttttgcaa tttggtttct tcttgcctct gctgacagcg     480
tggccaggcg actgcagtca cgtctccaac aaccaagttg tgttgcttga tacaacaact     540
gtactgggag agctaggatg gaaaacatat ccattaaatg ggtgggatgc catcactgaa     600
atggatgaac ataataggcc cattcacaca taccaggtat gtaatgtaat ggaaccaaac     660
caaaacaact ggcttcgtac aaactggatc tcccgtgatg cagctcagaa aatttatgtg     720
gaaatgaaat tcacactaag ggattgtaac agcatcccat gggtcttggg gacttgcaaa     780
gaaacattta atctgtttta tatggaatca gatgagtccc acggaattaa attcaagcca     840
aaccagtata caaagatcga cacaattgct gctgatgaga gttttaccca gatggatttg     900
ggtgatcgca tcctcaaact caacactgaa attcgtgagg tggggcctat agaaaggaaa     960
ggattttatc tggcttttca agacattggg gcgtgcattg ccctggtttc agtccgtgtt    1020
ttctacaaga aatgcccctt cactgttcgt aacttggcca tgtttcctga taccattcca    1080
agggttgatt cctcctcttt ggttgaagca cggggttctt gtgtgaagag tgctgaagag    1140
cgtgacactc ctaaactgta ttgtggagct gatggagatt ggctggttcc tcttggaagg    1200
tgcatctgca gtacaggata tgaagaaatt gagggttctt gccatgcttg cagaccagga    1260
ttctataaag ctttttgctgg aacacaaaa tgttctaaat gtcctccaca cagtttaaca    1320
tacatggaag caacttctgt ctgtcagtgt gaaaagggtt atttccgagc tgaaaaagac    1380
ccaccttcta tggcatgtac caggccacct tcagctccta ggaatgtggt ttttaacatc    1440
aatgaaacag cccttatttt ggaatggagc ccaccaagtg acacaggagg agaaaaagat    1500
ctcacataca gtgtaatctg taagaaatgt ggcttagaca ccagccagtg tgaggactgt    1560
ggtggaggac tccgcttcat cccaagacat acaggcctga tcaacaattc cgtgatagta    1620
cttgactttg tgtctcacgt gaattacacc tttgaaatag aagcaatgaa tggagtttct    1680
gagttgagtt tttctcccaa gccattcaca gctattacag tgaccacgga tcaagatgca    1740
ccttccctga taggtgtggt aaggaaggac tgggcatccc aaaatagcat tgccctatca    1800
tggcaagcac ctgctttttc caatggagcc attctggact acgagatcaa gtactatgag    1860
aaagaacatg agcagctgac ctactcttcc acaaggtcca agcccccag tgtcatcatc    1920
acaggtctta agccagccac caaatatgta tttcacatcc gagtgagaac tgcgacagga    1980
```

-continued

```
tacagtggct acagtcagaa atttgaattt gaaacaggag atgaaacttc tgacatggca    2040
gcagaacaag gacagattct cgtgatagcc accgccgctg ttgggggatt cactctcctc    2100
gtcatcctca ctttattctt cttgatcact gggagatgtc agtggtacat aaaagccaag    2160
atgaagtcag aagagaagag aagaaaccac ttacagaatg ggcatttgcg cttcccggga    2220
attaaaactt acattgatcc agatacatat gaagacccat ccctagcagt ccatgaattt    2280
gcaaaggaga ttgatccctc aagaattcgt attgagagag tcattggggc aggtgaattt    2340
ggagaagtct gtagtgggcg tttgaagaca ccagggaaaa gagagatccc agttgccatt    2400
aaaactttga aaggtggcca catggatcgg caaagaagag attttctaag agaagctagt    2460
atcatgggcc agtttgacca tccaaacatc attcgcctag aaggggttgt caccaaaaga    2520
tccttcccgg ccattggggt ggaggcgttt tgccccagct tcctgagggc agggttttta    2580
aatagcatcc aggccccgca tccagtgcca gggggaggat cttttgccccc caggattcct    2640 gctggcagac cagtaatgat tgtggtggaa tatatggaga atggatccct agactccttt    2700
ttgcggaagc atgatggcca cttcacagtc atccagttgg tcggaatgct ccgaggcatt    2760
gcatcaggca tgaagtatct ttctgatatg ggttatgttc atcgagacct agcggctcgg    2820
aatatactgg tcaatagcaa cttagtatgc aaagtttctg attttggtct ctccagagtg    2880
ctggaagatg atccagaagc tgcttataca acaactgacc tcttccaaac tctaacactt    2940
aacctctgct attctgcata aattctgaga aaagccaaat tttctgtcgg tctaagaaga    3000
catagcctac acccaactgg agataattat aaaaaataat gaagcagcat gaggggaagg    3060
tatttaatgt gtattttaaa gttgggagag attctccttc acctaattta ggtgtttgtg    3120
aattggcttg acttttgaa gttaatttt aagccttgaa catgtccaac tttaagaact    3180
ttaagaataa atattttaac acaagtgaaa aaaaaaaaa                           3220
```